United States Patent
Hookom et al.

(10) Patent No.: US 9,324,052 B2
(45) Date of Patent: Apr. 26, 2016

(54) SYSTEM, METHOD, AND APPARATUS FOR BARCODE IDENTIFICATION WORKFLOW

(71) Applicant: McKesson Financial Holdings, Hamilton (BM)

(72) Inventors: Jacob Hookom, Eden Prairie, MN (US); Marc Raymond, Burnsville, MN (US)

(73) Assignee: McKesson Medical-Surgical Minnesota Supply Inc., Golden Valley, MN (US)

( * ) Notice: Subject to any disclaimer, the term of this patent is extended or adjusted under 35 U.S.C. 154(b) by 77 days.

(21) Appl. No.: 14/228,584

(22) Filed: Mar. 28, 2014

(65) Prior Publication Data

US 2015/0278753 A1    Oct. 1, 2015

(51) Int. Cl.
- *G06K 7/14* (2006.01)
- *G06Q 10/08* (2012.01)
- *G06Q 50/22* (2012.01)

(52) U.S. Cl.
CPC ............ *G06Q 10/087* (2013.01); *G06K 7/1408* (2013.01); *G06K 7/1439* (2013.01); *G06K 7/1443* (2013.01); *G06Q 50/22* (2013.01)

(58) Field of Classification Search
USPC ............................................ 235/375, 462.07
See application file for complete search history.

(56) References Cited

U.S. PATENT DOCUMENTS

| | | | |
|---|---|---|---|
| 6,098,892 A * | 8/2000 | Peoples, Jr. | 235/494 |
| 7,770,797 B2 * | 8/2010 | Weiner et al. | 235/462.25 |
| 2006/0218026 A1 * | 9/2006 | Osborne | 705/8 |
| 2009/0066509 A1 * | 3/2009 | Jernstrom et al. | 340/568.1 |
| 2013/0105568 A1 * | 5/2013 | Jablonski et al. | 235/375 |
| 2015/0034713 A1 * | 2/2015 | Jones et al. | 235/375 |

* cited by examiner

*Primary Examiner* — Christle I Marshall
(74) *Attorney, Agent, or Firm* — Alston & Bird LLP

(57) ABSTRACT

A method, system, and corresponding apparatus are provided for translating components of a data set from a barcode to complete an information set. In particular, a method may include receiving a first data string corresponding to a first scanned barcode; decoding the first data string according to the first barcode format to generate a first data payload; and identifying, by a processor, from the first data payload a first set of rules for extracting information from the first data payload. Methods may include extracting information from the first data payload according to the first set of rules to obtain one or more components; translating the one or more components of the first data payload into at least one translated component; and providing for display of the at least one translated component.

20 Claims, 5 Drawing Sheets

Barcode Database 400

- Set 410
  - Expression 420
    - Component A 440
    - Component B 441
  - Expression 422
    - Component C 442
    - Component A 443
  - Expression 424
- Set 412
  - Expression 426
    - Component B 444
  - Expression 428
    - Component C 445
- Set 414
  - Expression 430
    - Component A 446
- Set 416
  - Expression 432
    - Component A 447
  - Expression 434
- Set 418
  - Expression 436

FIG. 4

SYSTEM, METHOD, AND APPARATUS FOR BARCODE IDENTIFICATION WORKFLOW

TECHNOLOGICAL FIELD

Exemplary embodiments of the present invention relate generally to capturing information from an identification code and, in particular, to capturing information from a barcode, establishing the type of information contained therein, and guiding a user to obtain additional barcode information in the event the information is incomplete.

BACKGROUND

In various fields of endeavor the identification of articles is important for tracking, auditing, and various other record keeping processes. In some fields, identification of an article may be necessary to establish a destination for the article, or to populate a record for a product that the article is to be associated with. Proper identification may be critical in some fields, such as in the field of medical transplants or implants. The identification of an implant that is to be used in a patient may be necessary for tracking the implant in studies, identifying potential candidates for implant recalls or consultations, or for registering an implant with a provider, manufacturer, or regulatory entity. The identification of implants, when performed manually by reading and transcribing identifying indicia, may introduce the opportunity for errors or omissions. Further, manual identification can be tedious and time consuming, particularly where the identification of an implant must be transcribed and communicated to various entities.

BRIEF SUMMARY

In general, exemplary embodiments of the present invention provide an improvement over the known prior art by, among other things, providing a system, method, and apparatus for capturing information from a barcode, establishing the type of information contained therein, and guiding a user to obtain additional information in the event the originally scanned information is incomplete.

In particular, according to one aspect of the present invention, a method is provided including receiving a first data string corresponding to a first scanned barcode; decoding the first data string according to the first barcode format to generate a first data payload; and identifying, by a processor, from the first data payload a first set of rules for extracting information from the first data payload. Methods may include extracting information from the first data payload according to the first set of rules to obtain one or more components; translating the one or more components of the first data payload into at least one translated component, where the at least one translated component may include, but is not limited to, a serial number, a model, or an expiration date; and providing for display of the at least one translated component. Methods may include causing the at least one translated component to be provided to at least one software program in response to the at least one translated component comprising a complete set of product information. The at least one software program may include at least one of an electronic medical record or a product registration program. The first set of rules for extracting information from the first data payload may include rules for parsing the first data payload into one or more components.

According to some embodiments, methods may include providing for display of an indication of additional information needed in response to the at least one translated component not comprising a complete set of product information. Providing for display of an indication of additional information needed may include providing for display of instructions to scan a second barcode. The instructions to scan a second barcode may include at least one of an identification of a location of the second barcode or a human-identifiable visual distinction of the second barcode. Methods may include receiving a second data string corresponding to a second scanned barcode; decoding the second data string according to a second barcode format to generate a second data payload; and identifying from the second data payload a second set of rules for extracting information from the second data payload. Embodiments may include extracting information from the second data payload according to the second set of rules to obtain one or more components; translating the one or more components of the second data payload into at least one second translated component, where the at least one second translated component may include, but is not limited to, the serial number, the model, or the expiration date; and providing for display of the at least one second translated component.

Example embodiments of the present invention may provide a computing device including processing circuitry configured to receive a first data string corresponding to a first scanned barcode; decode the first data string according to a first barcode format to generate a first data payload; and identify from the first data payload a first set of rules for extracting information from the first data payload. Embodiments of the computing device may be configured to extract information from the first data payload according to the first set of rules to obtain one or more components; translate the one or more components of the first data payload into at least one translated component, where the at least one translated component may include, but is not limited to, a serial number, a model, or an expiration date; and provide for display of the at least one translated component. Embodiment may also cause the at least one translated component to be provided to at least one software program in response to the at least one translated component including a complete set of product information. The at least one software program may include at least one of an electronic medical record program or a product registration program. The first set of rules for extracting information from the first data payload may include rules for parsing the first data payload into one or more components.

According to some embodiments, the computing device may include processing circuitry configured to provide for display of an indication of additional information needed in response to the at least one translated component not comprising a complete set of product information. The circuitry configured to provide for display of an indication of additional information needed may be configured to provide for display of instructions to scan a second barcode. The instructions to scan a second barcode may include at least one of an identification of a location of the second barcode or a human-identifiable visual distinction of the second barcode. The circuitry may further be configured to receive a second data string corresponding to a second scanned barcode; decode the second data string according to a second barcode format to generate a second data payload; and identify from the second data payload a second set of rules for extracting information from the second data payload. Methods may also extract information from the second data payload according to the second set of rules to obtain one or more components; translate the one or more components of the second data payload into at least one second translated component, where the at least one translated component may include, but is not limited to, the serial number, the model, or the expiration date; and provide for display of the at least one second translated component.

Embodiments of the present invention may provide a computer program product including a non-transitory computer readable storage medium having program code portions stored thereon, the program code portions configured, upon execution, to receive a first data string corresponding to a first scanned barcode. The program code portions may also be configured to decode the first data string according to a first barcode format to generate a first data payload; identify, from the first data payload, a first set of rules for extracting information from the first data payload; extract information from the first data payload according to the first set of rules to obtain one or more components; and translate the one or more components of the first data payload into at least one translated component. The at least one translated component may include, but is not limited to, a serial number, a model, or an expiration date. The program code portions may be configured, upon execution, to provide for display of the at least one translated component. The first set of rules for extracting information from the first data payload may include rules for parsing the first data payload into one or more components.

According to some embodiments, the program code portions may further be configured, upon execution, to cause the at least one translated component to be provided to at least one software program in response to the at least one translated component including a complete set of product information. The at least one software program includes at least one of an electrical medical record program or a product registration program. The program code portions may be configured, upon execution, to provide for display of an indication of additional information needed in response to the at least one translated component not including a complete set of product information. The program code portions, upon execution, to provide for display of an indication of additional information needed may include program code portions configured, upon execution, to provide for display of instructions to scan a second barcode.

According to some embodiments, the program code portions may be configured, upon execution, to receive a second data string corresponding to a second barcode; decode the second data string according to a second barcode format to generate a second data payload; and identify from the second data payload a second set of rules for extracting information from the second data payload. Embodiments may extract information from the second data payload according to the second set of rules to obtain one or more components; translate the one or more components of the second data payload into at least one second translated component, where the at least one second translated component may include, but is not limited to, the serial number, the model, or the expiration date; and provide for display of the at least one second translated component.

BRIEF DESCRIPTION OF THE DRAWINGS

Figure 1:
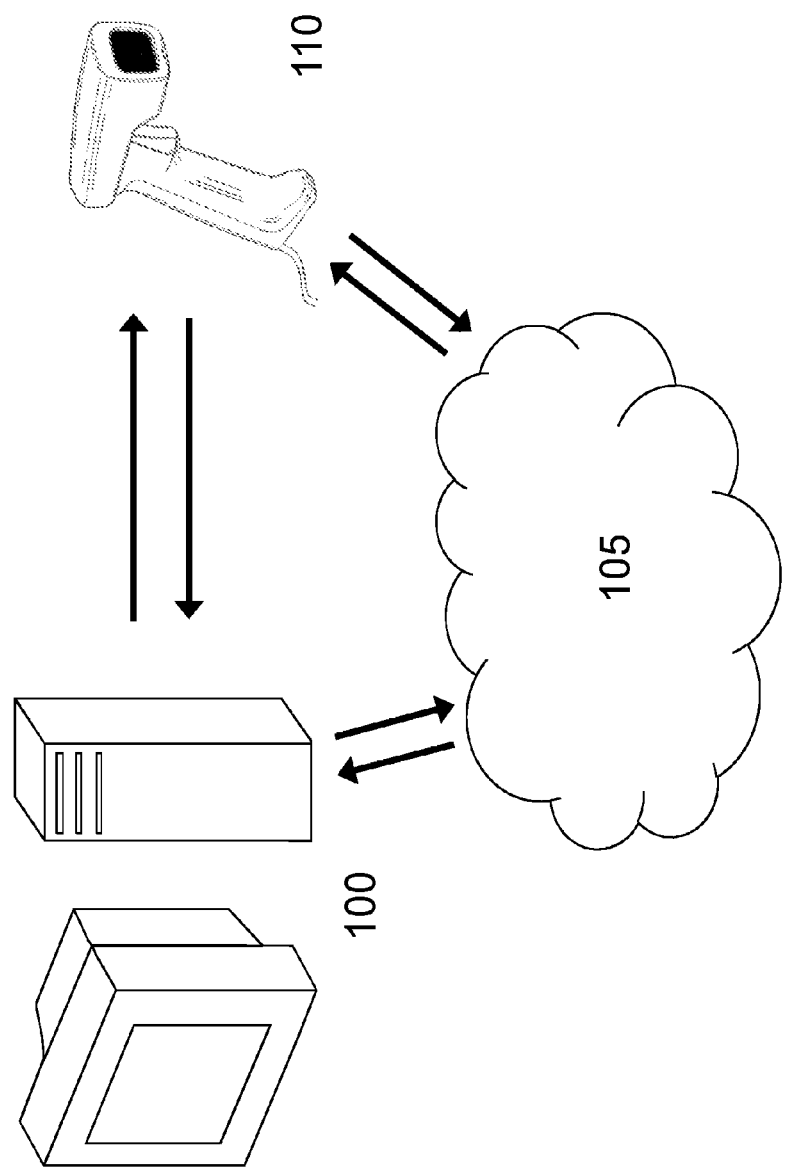
Figure 2:
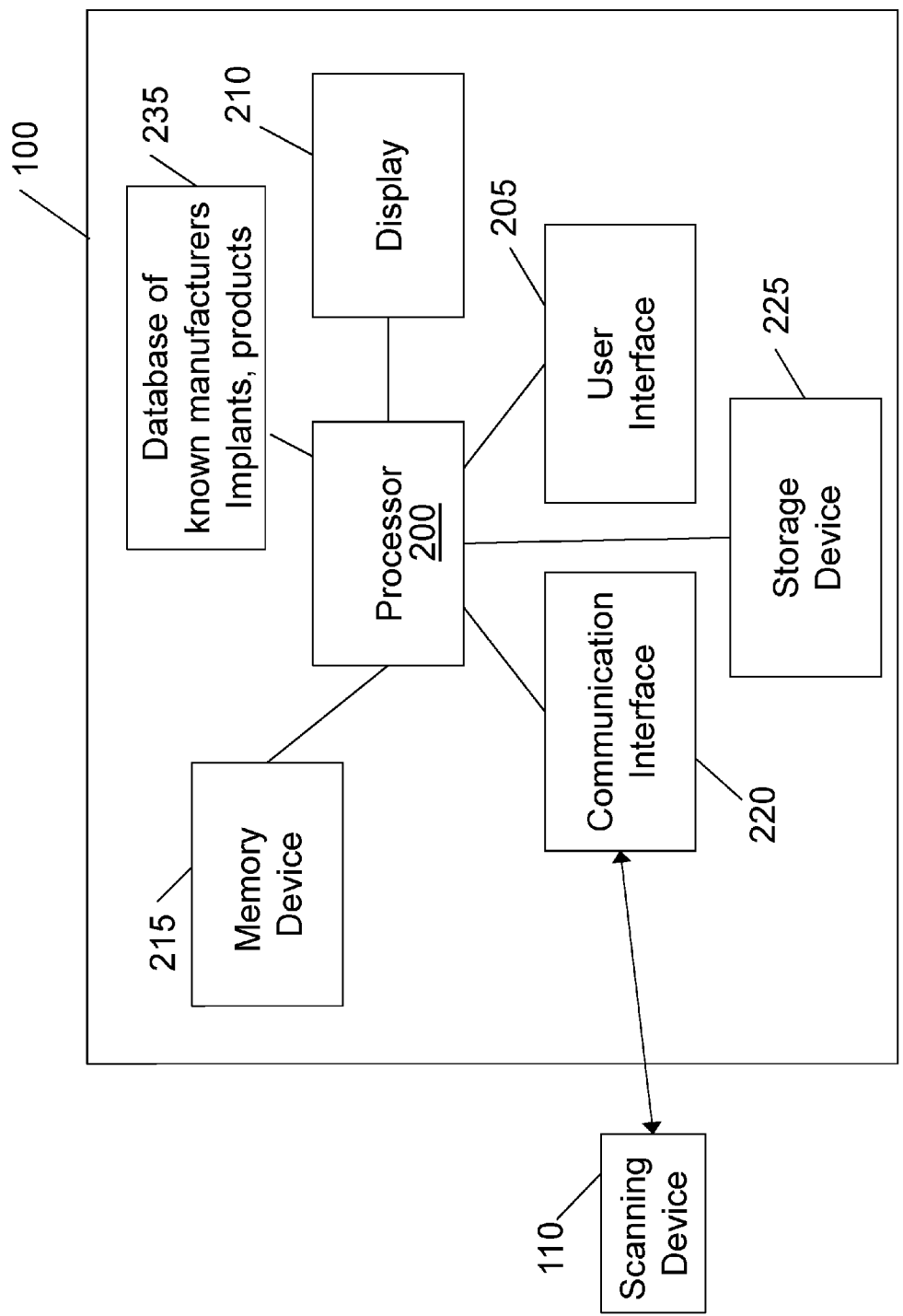
Figure 3:
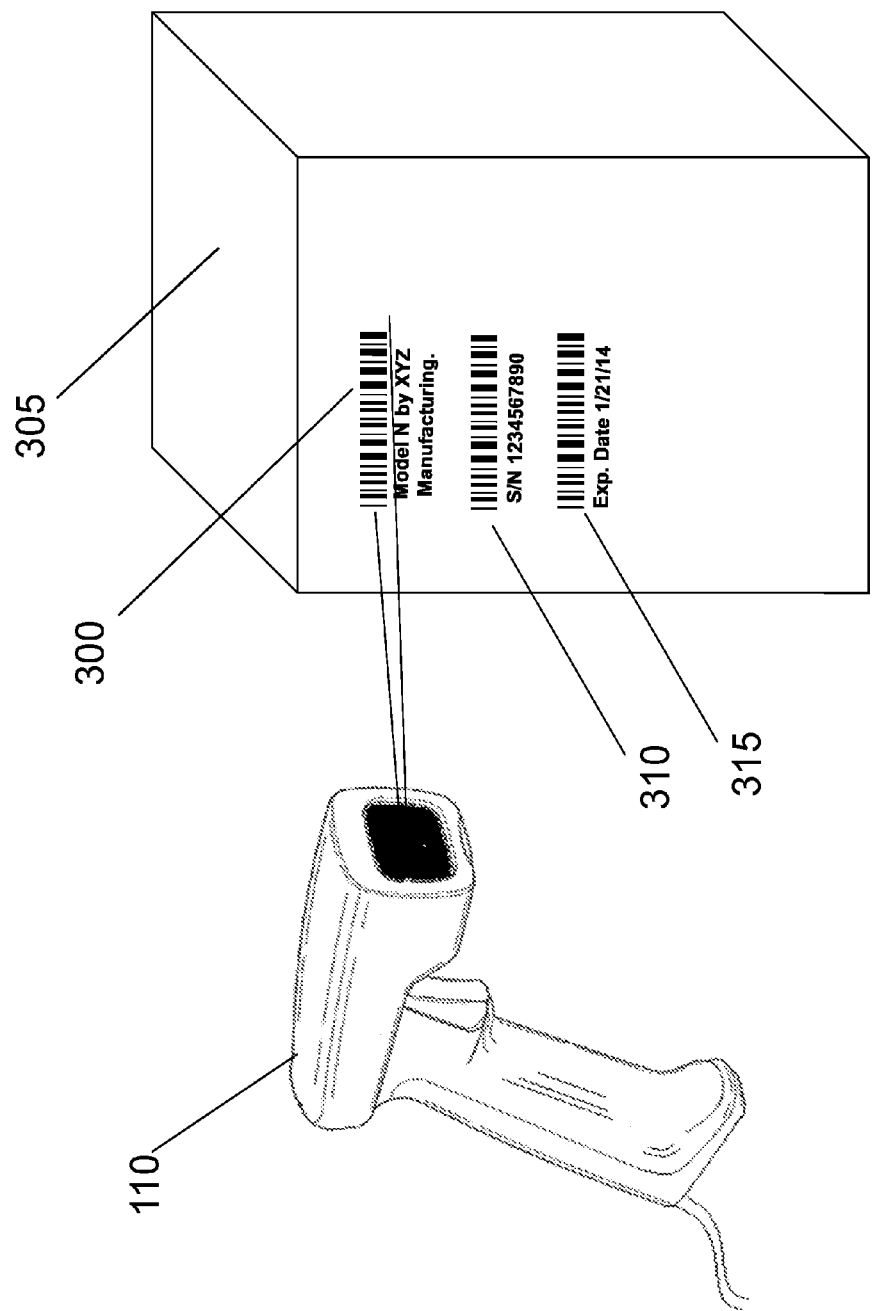
Figure 5:
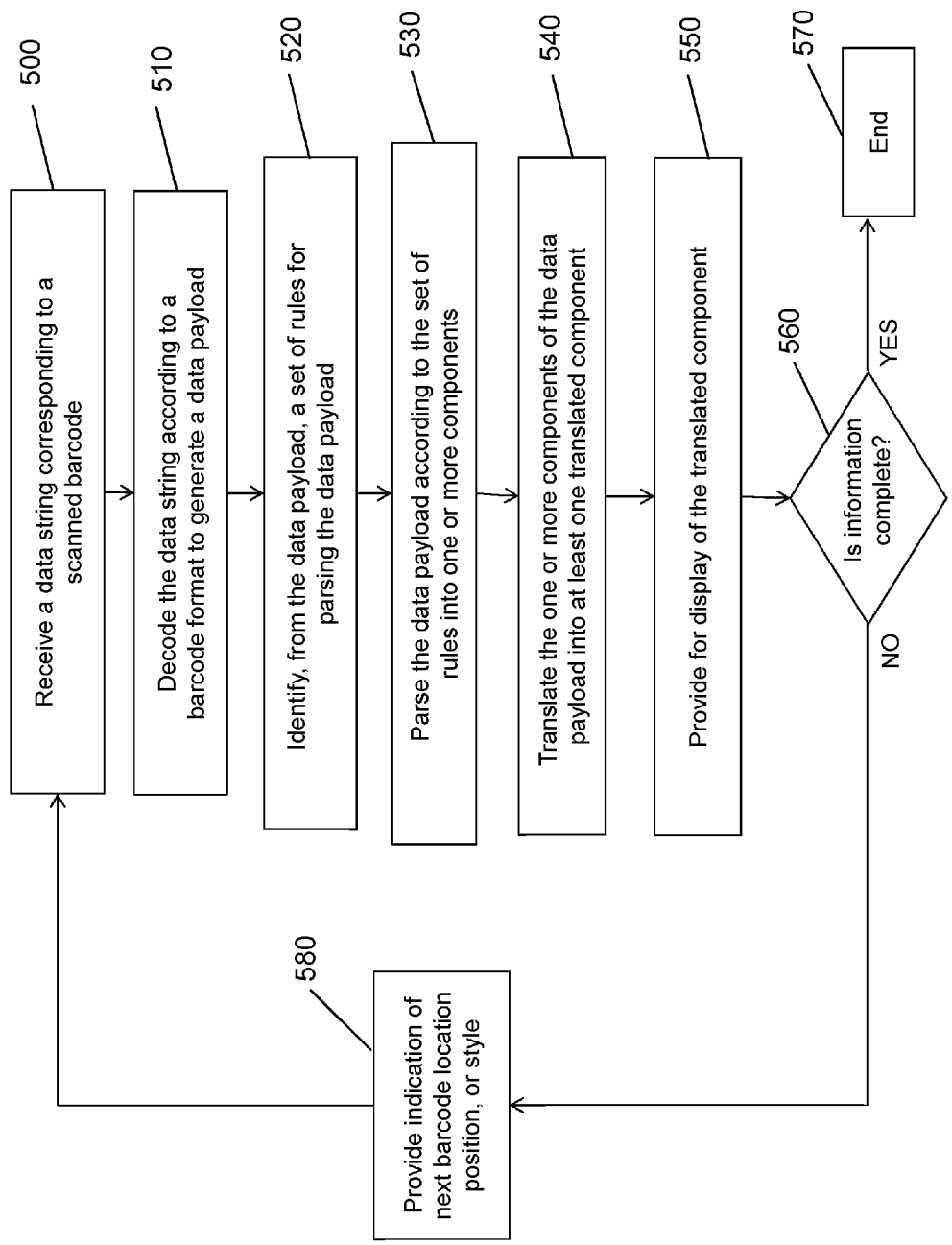

Having thus described certain example embodiments of the invention in general terms, reference will now be made to the accompanying drawings, which are not necessarily drawn to scale, and wherein:

FIG. 1 illustrates a system for translating components of a data set from a barcode to complete an information set according to an example embodiment of the present invention;

FIG. 2 is a block diagram of various components of a system for translating components of a data set from a barcode to complete an information set according to an example embodiment of the present invention;

FIG. 3 illustrates an example implementation of a system for translating components of a data set from a barcode to complete an information set according to the present invention;

FIG. 4 illustrates a graphical representation of translating components of a data set from a barcode to complete an information set according to an example embodiment of the present invention; and FIG. 5 is a flowchart of a method for translating components of a data set from a barcode to complete an information set according to an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

In general, example embodiments of the present invention provide a means for identifying an article by scanning a barcode, ascertaining a format for the scanned barcode, and decoding the barcode according to the determined format. A set of rules for interpreting the decoded barcode is determined based on the data payload of the decoded barcode, and information is extracted from the data payload. The information may be in the form of a component. Components include identifying information, which may include, but is not limited to, a serial number, model number, manufacturer, expiration date, etc. According to some embodiments, the component is extracted from the data payload by parsing the data payload into one or more components. Optionally, a component may be obtained through interpretation of the data payload, such as through an interpretation of a pattern or format. Whether the component is extracted by parsing the data payload or by otherwise interpreting the data payload, the rules for extracting the component from the data payload are identified from the data payload. The components are then assessed to determine if all of the information required is present. In the event additional information is needed, a user may be guided to collect additional information, such as through an additional barcode scan, to obtain the additional information. While embodiments of the present invention will be described with respect to the medical field, and the medical implant field in particular, it is appreciated that embodiments of the present invention may be implemented in various fields in which information must be decoded from one or multiple barcodes.

Implants used in surgical procedures generally require a set of documentation and identifying attributes to be recorded for regulatory reporting and for inventory management. Generally, this procedure is a paper-based process or electronic process that requires extensive manual data entry. The implant information captured must be used in multiple workflows including: receiving, billing/consignment management, regulatory reporting, and surgical documentation. Inefficiencies in capturing implant information are compounded by these multiple workflow touch points. Further, manual data entry can introduce opportunities for inaccuracies.

Presently, facilities may use a paper-based process for the registration of medical implant information which may require labels to be printed and attached to various documents before being physically mailed to a regulatory agency or to an implant manufacturer. Electronic inventory solutions may also be used to resolve some inefficiencies, but customers are left manually keying implant information into a generic solution. Even if the information is manually keyed and stored within the inventory system, the information for an inventory system may not be sufficient or in the proper format for medical implant reporting and regulatory use. Solutions involving barcoding in this space may be provided that are specific to a manufacturer and not a generalized solution that accommodates all manufacturers and products in the surgical space. Thus, an improved system is needed to overcome these deficiencies.

Described herein is a system, method, and apparatus for capturing information from a barcode, establishing the type of information encoded in the barcode, translating the information, and guiding a user to obtain additional information in the event the originally scanned information is incomplete.

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, magnetic storage devices, universal serial bus (USB) storage, solid state devices (e.g., flash memory), or the like.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of an identification system that can be used in conjunction with various embodiments of the present invention. As shown in FIG. 1, an example embodiment of the identification system may include a scanning device 110, one or more networks 105, and a processing device 100. As illustrated, the scanning device 110 may be in wired or wireless communication with one or both of the network(s) 105 and the processing device 100. Embodiments may further include other network entities from which data may be received from or transmitted to, as will be described further below. Each of the components of the system may be in electronic communication with, for example, one another over the same or different wireless or wired networks (e.g., network 105) including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

FIG. 2 illustrates the various components of an example embodiment of the identification system of FIG. 1, including the scanning device 110 which may be in communication with the processor 200 of, for example, the processing device 100. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an example embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the identification system may be configured to, among other things, to facilitate the accurate scanning and identification of medical implants as they are scanned ahead of use. A display 210 may be configured to present additional information to a user, such as confirming the scanned information contained some or all of the information needed from the medical implant, and to confirm the information gathered is correct. Further, the display 210 may be configured to guide a user to scan an additional barcode in the event that the information gathered from a first barcode scan did not provide all of the information necessary. The user interface 205 may include a touch screen, such as when the processing device is a tablet computer or portable computing apparatus or the user interface may include a keyboard and/or a pointing device, such as a mouse.

According to an example embodiment used in the medical field for medical implants, the identification system may further be in communication with a database of known manufacturers and implants 235 which may include identifying information regarding a plurality of implants, as described further below. In another example embodiment, this database may include manufacturers and/or product identifiers, together with rule metadata that may function to instruct the processor to parse information, such as the information from a barcode. While FIG. 2 shows the database 235 as part of the processing device 100, as one of ordinary skill in the art will appreciate, the database need not be integrated within the processing device 100 and may, instead, be external to and accessed by the processing device 100. The identification system may further include transitory and non-transitory memory device 215, which may include both random access memory (RAM) and read only memory (ROM). The ROM may be used to store a basic input/output system (BIOS) containing the basic routines that help to transfer information to the different elements within the identification system.

In addition, in one embodiment, the identification system may include at least one storage device 225, such as a hard disk drive, a CD drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, an audit trail of implants identified or mapped, operations, errors, alerts, and manual identification of implants or information components thereof as described below.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the identification system with the assistance of the processor 200 and operating system, although their functionality need not be modularized. In addition to the program modules, the identification system may store or be in communication with one or more databases.

Also located within the identification system, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the identification system 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the identification system components may be located remotely from other identification system components. For example the scanning device 110 may be located or in communication with a remote network entity. Furthermore, one or more of the components may be combined and additional components performing functions described herein may be included in the identification system.

According to an example embodiment of the present invention, a user may use an embodiment of the identification system described above to scan a first barcode 300 encoded on the packaging 305 of a medical implant, as illustrated in FIG. 3. While the embodiments disclosed herein describe and illustrate the scanning of a conventional barcode, it is appreciated that the product identification may be encoded onto a medication package through any available means, such as through a two-dimensional barcode, a three-dimensional barcode, or a Quick Response (QR) code. The scanning device 110 of example embodiments may be configured to read any of these available encoding means. As such, the embodiments illustrated herein are not intended to limit the mechanisms for encoding and reading the identification, but merely provide an example embodiment.

The scanning device 110, illustrated in FIG. 3, may send the data string corresponding to the scanned first barcode information to the processing device 100. The scanning device 110 may provide an interpretation of the data string of the scanned barcode, such as decoding the barcode into an alpha-numerical format, or the scanning device 110 may provide only interpreted scanned information to the processing device 100 for translation into the alpha-numeric format stored in the barcode. A first barcode format may be determined from the data string of the first scanned barcode, such as by the processing device 100. The first barcode format may include, for example, a Universal Product Code (UPC) barcode, Code-39 type barcode, EAN-8 type barcode, GS1-128 type barcode, High-Capacity Color 2-dimensional barcode, MaxiCode 2-dimensional barcode, QR code, or any available code format. The format may be determined based upon the indicators stored within the code itself, such as the shape, the start/stop patterns, and/or the finder pattern.

Once the barcode format for the data string corresponding to the first scanned barcode 300 is established, the data payload from the first scanned barcode may be obtained. The data payload is the data that is encoded into the barcode format. Different barcode formats may add guard codes, start/stop codes, checksums, or other information to help the processing device determine the format such that the data payload may be only a portion of the total barcode. Once the data payload is established from the data string, the processing system may then compare the barcode to a set of matching instruction sets which help identify the manufacturer and a set of rules on how to parse the data payload for all related information components.

The data payload may be of a particular format, or may include identifying information within the payload that identifies one or more of a manufacturer, a product, a model number, a serial number, etc. The format, or any identifying information contained within the barcode data payload may be used to establish a match between the data payload and a rules set or instruction set for how the data payload is to be parsed or otherwise interpreted. A plurality of rules sets or instruction sets may be stored, such as in database 235. The format or identifying information from the data payload may be compared against known formats or known identities in order to determine a rules set or instruction set that corresponds to the particular format or identifying information obtained from the data payload.

Once an instruction set or rules set is identified as corresponding to the data payload, the instructions or rules may be applied to the data payload. According to an example embodiment, the instruction set corresponding to a data payload may include instructions for extracting information from the data payload, such as by parsing the data payload into components. The components of the data payload may then be parsed according to the instructions to extract the components from the data payload. The components may subsequently be translated to obtain manufacturer and product identification through component translation. The translated components may include information such as a serial number, a model, an expiration date, etc. The data payload may optionally include a numerical value that may require formatting for proper interpretation. For example, an intraocular lens implant may include in the identifying information a diopter of the implant. The translated component parses the diopter in order to properly format the information, such as translating "255" into "25.5". Similarly, a date may be included in the data payload and may require parsing to extract a properly formatted date.

According to some embodiments, the instruction set matched to a particular data payload may indicate that the data payload does not include components into which the data payload may be parsed. The instruction set may instead indicate that the data payload is formatted in such a way as to extract the identity of the implant through the format of the barcode. In such an example, the data payload may correspond to the component and the instruction set may function to translate the data payload to obtain a translated component including the identifying information. In the above-described embodiments, the rule set or instruction set may provide a manner to extract identifying information from a data payload, whether the extraction includes parsing the data payload or interpreting the data payload in order to obtain one or more identifying components regarding the product or implant.

According to some embodiments of the present invention, a data payload may be matched to more than one set of instructions, and/or more than one manufacturer or product may be identified from the data payload. In such an embodiment, a list of the identified manufacturers, products, or information relating to the sets of instructions may be presented to a user for manual intervention in order to resolve the proper identification. In some instances, the results of the manual intervention may be stored for future reference to avoid requiring manual intervention when the same, or a similar implant is identified subsequently.

During the scanning operation described above, a user may be guided through the scanning and identification of a product. For example, a user may be prompted to scan a first barcode 300. This guidance may be provided, for example, through display 210 of the processing device 100. The display may indicate to a user a general location or style of barcode that is sought for the first scanned barcode. Upon scanning of the first barcode, the display 210 may present the information that was obtained from the translated components of the scanned barcode. The information may be presented for a user to confirm or authenticate, as needed.

According to some embodiments, the first scanned barcode may provide only a portion of the information needed to complete a registration or identification of a product, such as a medical implant. Forms of a workflow required by a healthcare facility, doctor, manufacturer, or regulatory agency may require a plurality of information fields to be completed, such as a manufacturer, product model, serial number, expiration date, manufacture date, etc. The plurality of information fields may not be satisfied by the information from the translated components of the first scanned barcode. In such an embodiment, additional barcodes may need to be scanned.

The processing device 100 may determine that additional information fields require completion after receiving the translated components of the first scanned barcode 300. The user may be prompted to scan one or more additional barcodes in order to obtain the necessary information. Based on the manufacturer, product, or other information received from the first scanned barcode, a user may be presented with an indication of the information that remains to be collected. Additionally, the user may be presented with information, such as a textual indication of a location or a graphic illustration of a location of a second barcode 310 on a package that needs to be scanned. The second barcode 310 may be in a particular location of a package, as identified on the display 210. Optionally, the second barcode may be on an item within the package, and the display 210 may indicate to a user where the second barcode is located.

In response to guiding a user to a second barcode to scan, the second barcode may be scanned by the user. The processing device 100 may receive a second data string corresponding to the second scanned barcode. The data string of the second scanned barcode may be decoded according to a format determined from the data string. The data payload from the second data string may be identified based on the decoded data string. As with the first scanned barcode, the second data payload may be parsed according to a second set of rules. The second set of rules for parsing the second data payload may be determined based on the second data payload, or alternatively, the second set of rules may be determined based on the information obtained from the first scanned barcode. For example, if the first scanned barcode identifies a particular manufacturer or product, the second set of rules for the second scanned barcode may be established based on the manufacturer or product. The second data payload may be parsed according to the second set of rules into one or more components. The one or more components may be translated to form one or more translated components, where the translated component can be one or more of a serial number, a model number, or an expiration date.

The translated components from the second scanned barcode may be used with the translated components of the first scanned barcode to populate the information fields requiring completion. The information may be presented on the display 210 for confirmation or approval by the user. If additional information fields still require information after receiving the translated components from the second scanned barcode, a user may be prompted to scan a third barcode, such as barcode 315 of FIG. 3, and the location of the third barcode may be indicated on the display. This may continue until all information to be obtained from the product packaging is received by the processing device 100.

Once a particular product, such as a medical implant, has been properly identified and all of the required information is obtained from the translated components, the information may be stored, for example, in the database of known manufacturers and implants. This database may store information that is common to other implants from other manufacturers, or information that is common to other manufacturers of the same implant. In this manner, information may be populated in the information fields from the database in response to identification of the implant or manufacturer, such as through a first barcode scan.

According to some example embodiments, a manufacturer may not provide barcodes for all required information. In such an embodiment, the processing device 100 may provide feedback to a user, such as through display 210, informing the user of the missing information required to complete the workflow. Some embodiments may provide a scan sheet, including a plurality of barcodes, relating to a particular field for which information was needed. For example, if a medical implant requires an expiration date, which may be based in part on the installation date, the expiration date may not be available on the implant packaging. In such an embodiment, a scan sheet may be provided including a barcode format date. The appropriate date may be selected and scanned by a user, thus fulfilling the requirement for the information needed for the workflow.

The aforementioned workflows for populating information fields from one or more scanned barcodes includes identifying a set of rules for parsing a data payload from the data string of a barcode. As noted above, the set of rules may be stored in a database, such as database 235 of FIG. 2. FIG. 4 illustrates a graphical representation of the parsing of a data payload of the data string of a scanned barcode. The barcode database 400 may function as a bridge between manufacturers and customer specific vendor applications. The barcode database may include a plurality of barcode Instruction Sets 410, 412, 414, for a particular manufacturer. These barcode Instruction Sets 410, 412, 414, may include a set of rules for one or more product models, such as medical implant models, where the expressions within the configuration may be collectively applicable. Each scanned barcode may be represented by an expression, such as Expressions 420-436, where the expression is a generalized pattern representing the data payload from a scanned barcode. With reference to the above example embodiments, the expression includes the rules that identify components within the expression or data payload. Further, the rules indicate which portion of an instruction set an expression or data payload represents. For example, an instruction set (e.g., Instruction Set 410) may dictate that a complete set of information includes a model number component, a serial number component, and an expiration date component. The instruction set may further include rules on how a barcode data payload understood and parsed to extract the components. According to the illustrated embodiment of FIG. 4, the Expression 420 includes Component A 440 and Component B 441 of the Instruction Set 410. In order to obtain Component C 442 of Instruction Set 410, a second data payload corresponding to expression 422 must be obtained from another barcode that is to be scanned. Upon scanning of the barcode containing Component C 442, and the extraction of Component C 442 from the data payload of the barcode according to Expression 422, the Instruction Set 410 is complete. While the Instruction Set 410 required two barcodes to be scanned to obtain all of the components of the set, Instruction Set 412 would require three barcodes to be scanned, corresponding to Expressions 424, 426, and 428, to obtain Components A, B, and C (443-445). Instruction Set 414 requires only a single barcode expression to be scanned to obtain the only component of the instruction set.

As outlined above, some data payloads from some barcodes may not include components that are parsed from the data payload. Instruction Set 416 includes two Expressions 432 and 434, where the first Expression 432 corresponds to a barcode with a data payload from which Component A 447 is extracted. The second Expression 434 corresponds to a barcode with a data payload that does not include a component that is parsed therefrom, but instead the Expression 434 realizes identifying information from the data payload according to Instruction Set 416. Similarly, Instruction Set 418 includes a single Expression 436 that corresponds to a barcode with a data payload from which no component is parsed, but instead the data payload is interpreted according to Expression 436 to obtain the necessary identifying information to form a translated component.

FIG. 5 illustrates an example embodiment of a method for obtaining a complete set of information components from a package. A data string corresponding to a scanned barcode may be received at 500. The data string may be decoded according to a barcode format to generate a data payload at 510. At 520, a set of rules for parsing the data payload may be identified from the data payload, and the data payload may be parsed according to these rules into one or more components at 530. The one or more components of the data may be translated into one or more translated components at 540, and the translated component may be provided for display at 550. At 560 a determination may be made as to whether the information is complete (e.g., is the data set complete). If so, then the routine may end at 570. If the information is incomplete, a user may be provided with an indication of the next barcode to be scanned at 580. The next barcode may be decoded, parsed, and translated as outlined in 500-550 until the information is complete.

In an example embodiment, an apparatus for performing the method of FIG. 5 above may include a processor (e.g., the processor 200) configured to perform some or each of the operations (500-580) described above. The processor 200 may, for example, be configured to perform the operations (500-580) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 500-580 may comprise, for example, the processing device 100 (or respective different components thereof). Additionally or alternatively, at least by virtue of the fact that the processor 200 may be configured to control or even be embodied as the processing system, the processor 200 and/or a device or circuitry for executing instructions or executing an algorithm for processing information as described above may also form example means for performing operations 500-580.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
receiving a first data string corresponding to a first scanned barcode;
decoding the first data string according to a first barcode format to generate a first data payload;
identifying, by a processor, from the first data payload a first set of rules for extracting information from the first data payload;
extracting information from the first data payload according to the first set of rules to obtain one or more components;

translating the one or more components of the first data payload into at least one translated component; and providing for display of the translated component.

2. The method of claim 1, further comprising:

causing the at least one translated component to be provided to at least one software program in response to the at least one translated component comprising a complete set of product information.

3. The method of claim 1, wherein the first set of rules for extracting information from the first data payload include rules for parsing the first data payload into one or more components.

4. The method of claim 1, further comprising:

providing for display of an indication of additional information needed in response to the at least one translated component not comprising a complete set of product information.

5. The method of claim 4, wherein providing for display of an indication of additional information needed comprises providing for display of instructions to scan a second barcode.

6. The method of claim 5, further comprising:

receiving a second data string corresponding to a second scanned barcode;

decoding the second data string according to a second barcode format to generate a second data payload;

identifying from the second data payload a second set of rules for extracting information from the second data payload;

extracting information from the second data payload according to the second set of rules to obtain one or more components;

translating the one or more components of the second data payload into at least one second translated component; and providing for display of the at least one second translated component.

7. The method of claim 1, wherein the first set of rules for extracting information from the first data payload includes an instruction set, wherein the instruction set dictates information elements required for a complete set of information.

8. The method of claim 7, wherein in response to the first data payload not including all of the information elements required for the complete set of information, providing for an indication of an instruction to scan a second barcode.

9. The method of claim 1, further comprising:

storing the at least one translated component of the first data payload;

receiving a second data string corresponding to a second scanned barcode;

decoding the second data string according to a second barcode format to generate a second data payload;

identifying, by the processor, from the second data payload, a second set of rules for extracting information from the first data payload;

extracting information from the first data payload according to the first set of rules to obtain one or more components;

translating the one or more components of the second data payload into at least one translated component;

determining if any information elements are missing from the at least one translated component of the second data payload; and retrieving at least one of the at least one translated component of the first data payload corresponding to the missing information elements from the at least one translated component of the second data payload.

10. A computing device comprising processing circuitry configured to:

receive a first data string corresponding to a first scanned barcode;

decode the first data string according to a first barcode format to generate a first data payload;

identify, from the first data payload a first set of rules for extracting information from the first data payload;

extracting information from the first data payload according to the first set of rules to obtain one or more components;

translate the one or more components of the first data payload into at least one translated component; and provide for display of the at least one translated component.

11. The computing device of claim 10, wherein the circuitry is further configured to:

cause the at least one translated component to be provided to at least one software program in response to the at least one translated component comprising a complete set of product information.

12. The computing device of claim 11, wherein the at least one software program comprises at least one of an electronic medical record program or a product registration program.

13. The computing device of claim 10, wherein the circuitry is further configured to:

provide for display of an indication of additional information needed in response to the at least one translated component not comprising a complete set of product information.

14. The computing device of claim 13, wherein the circuitry configured to provide for display of an indication of additional information needed comprises circuitry configured to provide for display of instructions to scan a second barcode.

15. The computing device of claim 14, wherein the instructions to scan a second barcode comprise at least one of an identification of a location of the second barcode or a human-identifiable visual distinction of the second barcode.

16. The computing device of claim 14, wherein the circuitry is further configured to:

receive a second data string corresponding to a second scanned barcode;

decode the second data string according to a second barcode format to generate a second data payload;

identify from the second data payload a second set of rules for extracting information from the second data payload;

extract information from the second data payload according to the second set of rules to obtain one or more components;

translate the one or more components of the second data payload into at least one second translated component; and provide for display of the at least one second translated component.

17. A computer program product comprising a non-transitory computer readable storage medium having program code portions stored thereon, the program code portions configured, upon execution, to:

receive a first data string corresponding to a first scanned barcode;

decode the first data string according to a first barcode format to generate a first data payload;

identify from the first data payload a first set of rules for extracting information from the first data payload;

extract information from the first data payload according to the first set of rules to obtain one or more components;

translate the one or more components of the first data payload into at least one translated component; and provide for display of the at least one translated component.

18. The computer program product of claim 17, wherein the program code portions are further configured, upon execution, to:

provide for display of an indication of additional information needed in response to the at least one translated component not comprising a complete set of product information.

19. The computer program product of claim 18, wherein the program code portions configured, upon execution, to provide for display of an indication of additional information needed comprise program code portions configured, upon execution, to provide for display of instructions to scan a second barcode.

20. The computer program product of claim 19, wherein the program code portions are further configured, upon execution, to:

receive a second data string corresponding to a second scanned barcode;

decode the second data string according to a second barcode format to generate a second data payload;

identify from the second data payload a second set of rules for extracting information from the second data payload;

extract information from the second data payload according to the second set of rules to obtain one or more components;

translate the one or more components of the second data payload into at least one second translated component; and provide for display of the at least one second translated component.

* * * * *